United States Patent
Yang et al.

(10) Patent No.: US 6,333,632 B1
(45) Date of Patent: Dec. 25, 2001

(54) ALTERNATING CURRENT DISCHARGE IONIZATION DETECTOR

(75) Inventors: Wenjun Yang, Sunnyvale; Peter C. Hsi, Fremont, both of CA (US)

(73) Assignee: RAE Systems, Inc., Sunnyvale, CA (US)

( * ) Notice: Subject to any disclaimer, the term of this patent is extended or adjusted under 35 U.S.C. 154(b) by 0 days.

(21) Appl. No.: 09/397,624

(22) Filed: Sep. 16, 1999

(51) Int. Cl.$^7$ .................................................. G01N 27/62
(52) U.S. Cl. ........................ 324/464; 324/459; 324/71.1
(58) Field of Search .................................. 324/464, 459, 324/468, 470, 465, 466, 71.1, 392, 455, 54

(56) References Cited

U.S. PATENT DOCUMENTS

| | | | |
|---|---|---|---|
| 4,028,617 | 6/1977 | Kamo et al. .......................... 324/33 |
| 4,266,196 | 5/1981 | Kawazoe et al. ..................... 324/464 |
| 4,447,728 | 5/1984 | Stafford et al. ................... 250/423 R |
| 4,609,875 | 9/1986 | Jeffers ................................ 324/464 |
| 4,789,783 | 12/1988 | Cook ................................... 250/379 |
| 4,975,648 | 12/1990 | Lawson et al. ..................... 324/464 |
| 4,994,748 | * 2/1991 | Rasulev et al. ..................... 324/468 |
| 5,086,254 | 2/1992 | Wells ............................. 315/111.21 |
| 5,153,519 | 10/1992 | Wentworth et al. ................. 324/464 |
| 5,192,865 | 3/1993 | Zhu ..................................... 250/288 |
| 5,317,271 | 5/1994 | Wentworth et al. ................. 324/464 |
| 5,394,090 | 2/1995 | Wentworth et al. ................. 324/464 |
| 5,394,091 | 2/1995 | Wentworth et al. ................. 324/464 |
| 5,394,092 | 2/1995 | Wentworth et al. ................. 324/464 |
| 5,541,519 | 7/1996 | Stearns et al. ....................... 324/464 |
| 5,889,404 | * 3/1999 | Abdel-Rehman et al. .......... 324/464 |
| 5,925,819 | 7/1999 | Yoshinaga et al. ................. 73/117.3 |
| 6,104,195 | * 8/2000 | Yoshinaga et al. ................. 324/459 |

OTHER PUBLICATIONS

Written Opinion dated Jul. 18, 2001 for corresponding PCT Application No. PCT/US00/25579.

* cited by examiner

Primary Examiner—Safet Metjahic
Assistant Examiner—T. R. Sundaram
(74) Attorney, Agent, or Firm—Skjerven Morrill MacPherson LLP; David W. Heid (57) ABSTRACT

A discharge ionization detector (DID) includes a sensor that uses an alternating current (AC) discharge through a working gas as an ionization source. The sensor includes a discharge chamber, into which the working gas is introduced, and an ionization chamber, into which a sample gas is introduced. UV photons from the discharge chamber and metastable particles that enter the ionization chamber from the discharge chamber ionize molecules in the sample gas. The ions generated from the ionized sample gas are measured as a current indicating the quantity of ionizable molecules in the sample gas. For selective identification of molecules in the sample gas, one or more chemical filters can filter the sample gas to separate target gases from gases that interfere with detection of the target gases. Additionally, a supply for the working gas can change the working gas to change the maximum energy available for ionization of the sample gas. Thus, current measurements with different working gases indicate quantities of classes of molecules having different ionization potentials.

26 Claims, 5 Drawing Sheets

ALTERNATING CURRENT DISCHARGE IONIZATION DETECTOR

BACKGROUND

1. Field of the Invention

This invention relates to an ionization detector using an alternating current (AC) discharge through a working gas as an ionization source for detection of ionizable gases.

2. Description of Related Art

The monitoring of the concentrations of volatile organic compounds (VOCs) and inorganic gases such as ammonia, phosphine, nitrogen oxides, and halogens is important in industrial applications. For such monitoring, a number of gas detectors have been developed.

A photo-ionization detector (PID) can monitor ionizable gases in air without separating the gases. The ionization potentials (IPs) of most VOCs and some inorganic gases are lower than the ionization potentials of the common components of air. For example, nitrogen, oxygen, water vapor, and carbon dioxide, which are the most common components of air, have ionization potentials of 15.58, 12.07, 12.61, and 13.77 eV, respectively, and the IPs of most of the VOCs are less than 12.0 eV. Accordingly, a PID can use an ionization source having maximum photon energy between 12 eV and the IP of a target gas to detect the target gas without ionizing the common components of air.

A common PID uses a sealed vacuum or low pressure lamp to generate UV photons. The UV photons pass through an optical window into an ionization chamber and ionize molecules having ionization potentials below the maximum photon energy of the lamp. After the ionization, one or more measuring electrodes of the PID measure the ion current that the ionized gas molecules cause. The measured current indicates the concentration of ionizable molecules in ionization chamber. One significant disadvantage of PIDs is the relatively short life of the UV lamp caused by window material deterioration, gas leakage into or from the lamp, and window surface contamination.

A flame ionization detector (FID) uses a chemical flame as an ionization source. A typical FID burns a working gas such as hydrogen in air. FIDs have several disadvantages that prevent their use as portable gas monitors. In particular, a FID requires a hydrogen source that must be replenished after a relatively short period of use. Typically, maintaining an adequate flame requires a minimum flow rate of about 15 ml/min of hydrogen. At that flow rate, hydrogen in a 75 ml cylinder with pressure of 1,800 psi can only sustain the flame for about 8 hours. Further, hydrogen presents the danger of an explosion. Also, the hydrogen-oxygen flame is a natural flame that has a directional effect on both baseline and span signals of the FID.

A discharge ionization detector (DID) is another device for measuring levels of VOCs and inorganic gases. A DID applies a high voltage across discharge electrodes to create an electric discharge or spark in a discharge chamber filled with an inert gas such as helium. The electric discharge through the inert gas creates active species such as UV photons and excited atoms. The active species that enter an ionization chamber containing a sample gas ionize components of the sample gas.

U.S. Pat. Nos. 4,028,617; 4,266,196; 4,789,783; and 4,975,648 which are incorporated here by reference in their entireties, describe DIDs having a DC discharge as ionization source. Papers by Jin et al. (J. Chromatograph. A, 761, p. 169, 1996, and Microchem. J., 52, p. 139, 1995), which are incorporated here by reference in their entireties, also describe DIDs using DC discharge. The known DIDs have problems with anode sputtering and contaminant deposition on the surfaces of discharge electrodes. The sputtering and deposition change the discharge electrodes and reduce reproducibility and long term stability of the DID.

U.S. Pat. Nos. 5,153,519; 5,317,271; 5,394,090; 5,394,091; 5,394,092; and 5,541,519, which are incorporated here by reference in their entireties, disclose pulsed DC DIDs. Pulsed DC discharge, in which the discharge is intermittent, can reduce the anode sputtering. However, the direction of the discharge electric field is constant, and anode sputtering and cathode contamination remain concerns.

U.S. Pat. No. 5,086,254, which is incorporated here by reference in its entirety, describes the application of a microwave induced plasma as an ionization source. A paper by Jin et al. (Microchem. J., 35(3), p281, 1987), which is incorporated here by reference in its entirety, introduces a surfatron-based microwave plasma as an ionization source for an ionization detector. The direction of the microwave electric field alternates, which solves the problems of anode sputtering. However, this detector requires a microwave generator and a special microwave transmission line, which make the detector more complicated and less portable. Further, microwave systems require a relatively large amount of power and have not been used in portable detectors.

The above-described DIDs and microwave-driven detectors are conventionally detectors for gas chromatography and have not been used for real-time gas monitoring. Most conventional DIDs use helium as a discharge gas. Basically, UV photons generated by an electric discharge through helium are a universal ionization source for gas chromatography detection because helium has high IP (24.58 eV). Photons from helium typically ionize all species of molecules in the sample gas. This is fine for gas chromatography because a gas chromatographic column separates the different constituents of a gas sample for separate ion current measurements. However, electric discharge in helium is not a suitable ionization source when monitoring VOCs and other contaminants in air because both the contaminants and the components of air are ionized.

U.S. Pat. Nos. 4,447,728 and 5,192,865, which are incorporated here by reference in their entireties, respectively disclose a discharge ionizer for mass spectrometry and an inductively coupled discharge combined with mass spectrometry. However, these systems are for fixed mass spectrometric systems, not for DIDs.

U.S. Pat. No. 4,609,875, which is incorporated here by reference in its entirety, discloses a real-time halogen gas detector that measures the variation of discharge current when a sample gas passes through the discharge region of a negative DC corona discharge. However, in actual use of such a detector, the sample gas would significantly contaminate the electrodes, and as a result, the long-term stability of the electrodes would be questionable.

A detector is sought that is suitable for portable use performing real-time measurements of contaminants in air and that avoids the problems of windows in PIDs, avoids the short operating times and explosion risks in FIDS, and avoids the stability problems associated with electrodes in conventional DIDs.

SUMMARY

In accordance with an aspect of the present invention, a real-time detector uses an alternating current (AC) discharge as a photo-ionization source when monitoring the content of a sample gas. The detector includes a discharge chamber, into which a working gas flows and an electric discharge is established, and an ionization chamber, into which a sample gas containing the ionizable gas is introduced. The working gas flows from the discharge chamber into the ionization chamber to prevent or suppress the flow of molecules of the sample gag into the discharge chamber.

The detector further includes discharge electrodes in the discharge chamber, and collecting and bias electrodes in the ionization chamber. An AC discharge passes between the discharge electrodes and through the working gas creates active species such as UV photons and metastable atoms and molecules of the working gas. These active species enter the ionization chamber from the discharge chamber and ionize ionizable molecules in the ionization chamber. The bias electrodes accelerate the ions formed in the ionization chamber toward the collecting electrode, and the collecting electrode collects the ions generated from the ionized gas.

The working gas is typically an inert gas, such as helium, argon, krypton, or xenon. In one embodiment of the invention, a supply of working gas selects from among a set of different working gases for measuring different target gases. The selection of working gases allows selection of different active species and selective identification of target gases by ion potential. For further selectivity in measurement, one or more chemical filters can be selected and used to isolate a particular target gas from other components that may be found in a sample gas.

The discharge electrodes are typically made of a noble metal such as platinum and gold, or are coated with the noble metal. The bias and collecting electrodes are typically a metal such as stainless steel. The collecting electrode is coupled to an electrometer that measures a current from the collected ions. One embodiment of the detector further includes a grounding electrode between the discharge chamber and the ionization chamber to stop ions from the AC discharge from entering the ionization chamber. The grounding electrode also prevents the AC discharge from interfering with the ionization of the sample gas in the ionization chamber.

A sample gas inlet provides the sample gas. A smaller portion of the sample gas flows through a first channel into the ionization chamber, and a larger portion of the sample gas flows through a second channel and is exhausted. The first channel radially or coaxially introduces the sample gas into the ionization chamber.

The detector may still further include a light detector that monitors the light intensity from the AC discharge. A control system monitors the light intensity and can change the AC voltage of the discharge to stabilize the production of active species.

BRIEF DESCRIPTION OF THE DRAWINGS

Use of same reference symbols in different figures indicates similar or identical items.

DESCRIPTION OF THE PREFERRED EMBODIMENTS

In accordance with an aspect of the invention, an ionization gas detector uses an alternating current (AC) discharge to provide an ionization source when monitoring volatile organic compounds (VOCs) and some inorganic gases in air. This kind of ionization gas detector is referred to herein as an alternating current discharge ionization detector (ACDID). The detector has a low flow rate of a working gas and is suitable for both portable and stationary applications.

Figure 1:
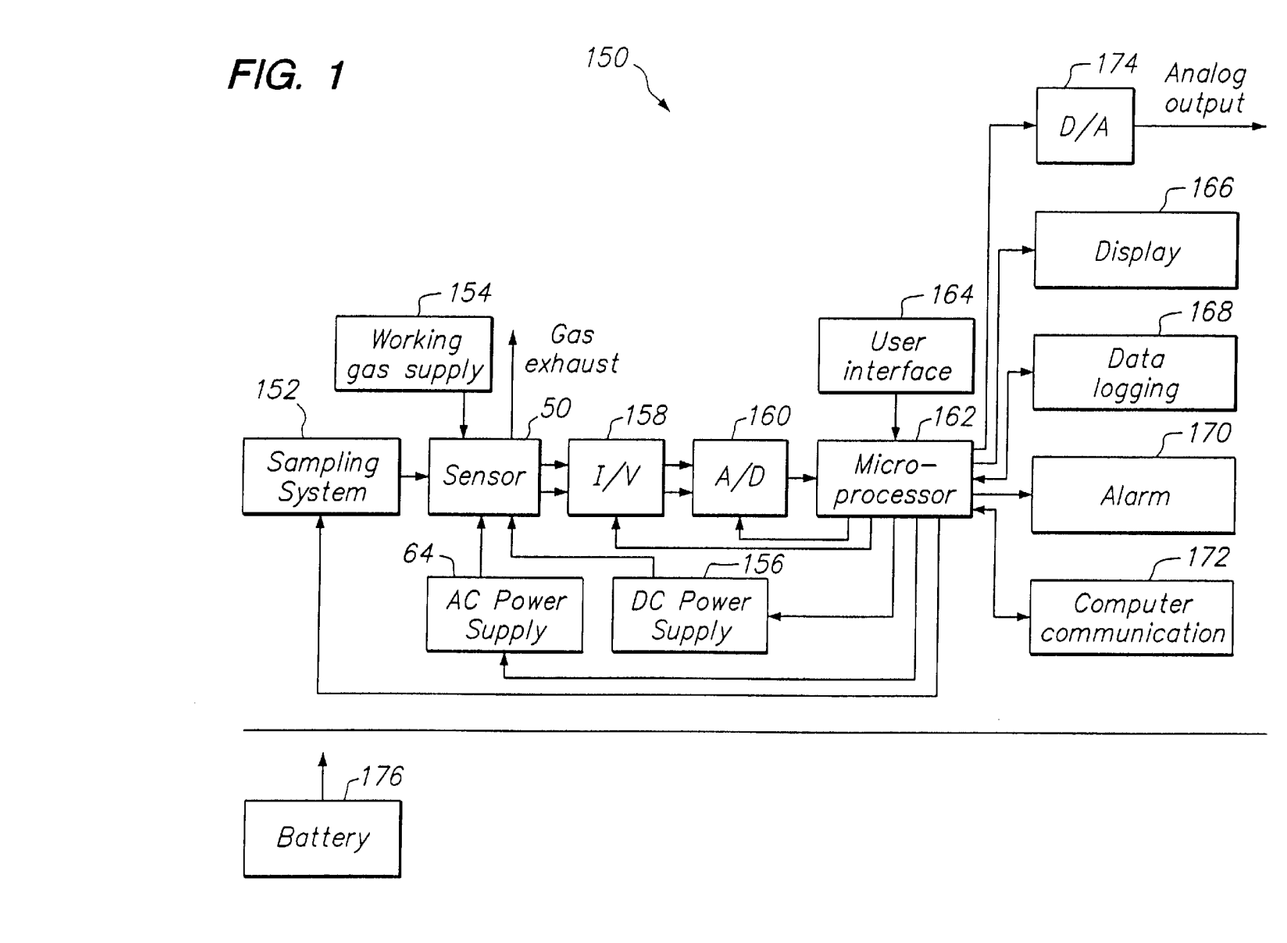
FIG. 1 is a block diagram of an alternating current discharge ionization detector (ACDID) in accordance with an embodiment of the invention.

FIG. 1 is a block diagram of an ACDID 150 in accordance with an embodiment of the invention. ACDID 150 includes a sensor 50 connected to a sampling system 152, a working gas supply 154, an AC power supply 64, and a DC power supply 156. Embodiments of sensor 50 are described further below with reference to FIGS. 2A, 2B, 2C, and 2D.

In the operation of ACDID 150, sampling system 152 supplies to sensor 50 a sample gas, which may include the target gas to be detected. Sampling system 152 can be a pneumatic system that circulates air from the surrounding ambient through sensor 50 as the sample gas. Alternatively, sampling system 152 can include a gas chromatographic column, a filtration system, or any other system for introducing a sample gas into sensor 50.

Working gas supply 154 supplies a working gas to sensor 50. Typical working gases include an inert gas such as helium, neon, argon, krypton, or xenon. Working gas supply 154 typically includes one or more canisters containing one or more working gases and valves that control the flow of working gas to sensor 50.

In sensor 50, an AC electric discharge through the working gas creates active species that can ionize target gases in the sample gas. AC power supply 64 is a high voltage AC power supply that powers the electric discharge in sensor 50. The electric discharge through the working gas creates ions, electrons, photons, and metastable atoms and molecules of the working gas. The UV photons and species in metastable excited states are ionizing agents that can enter an ionization chamber in sensor 50 to interact with and ionize the target gases which may be in the sample gas. DC power supply 156 applies bias voltages to the electrodes of sensor 50 so that the collector electrode collects ions from the sample gas for measurement of the current corresponding to the ions.

To transfer a current signal from sensor 50, ACDID 150 further includes a current-to-voltage (I/V) converter 158 and analog-to-digital (A/D) converter 160. The combination of I/V converter 158 and A/D converter 160 sends to a microprocessor 162 a digital signal indicating the ion current measured in sensor 50. Microprocessor 162 executes a suitable firmware routine to convert the measured current into a measured value representing a concentration of detected ionizable molecules in the sample gas.

For information input and output, microprocessor 162 interacts with a user interface 164, a display unit 166, a data logging unit 168, an alarm 170, a computer communication unit 172, and a digital-analog (D/A) converter 174. Display 166, which is typically an LCD or another suitable display device, indicates the measured value. If the measured value is above a threshold, microprocessor 162 activates alarm 170 which generates an audible, visual, or tactile signal to warn a user that the target gas is at levels above the threshold. Data log 168 periodically records the measured values that can be subsequently down loaded or processed for determination of accumulated exposure to target gases. Computer communication interface 172 permits down loading of information, for example, from data log 168 and up loading of operating parameters or instructions for microprocessor 162. D/A converter 174 allows analog output according to the software that microprocessor 162 executes.

A user can communicate with microprocessor 162 through user interface 164, which can be a set of buttons or a touch sensitive display. Microprocessor 162 controls the signal conversions in I/V converter 158, A/D converter 160 and D/A converter 174, and the data sent to display unit 166, data logging unit 168, alarm 170, and computer communication unit 172. Microprocessor 162 also controls sampling system 152, working gas supply 154, AC power supply 64, and bias voltage power supply 156 for operation of sensor 50.

For a portable application, a battery 176 powers ACDID 150. This allows a user to carry ACDID 150 for measurement of personal exposure to target gases. Alternatively, ACDID 150 is also suitable for stationary applications, for example, with a gas chromatographic column in sampling system 152.

Figure 2A:
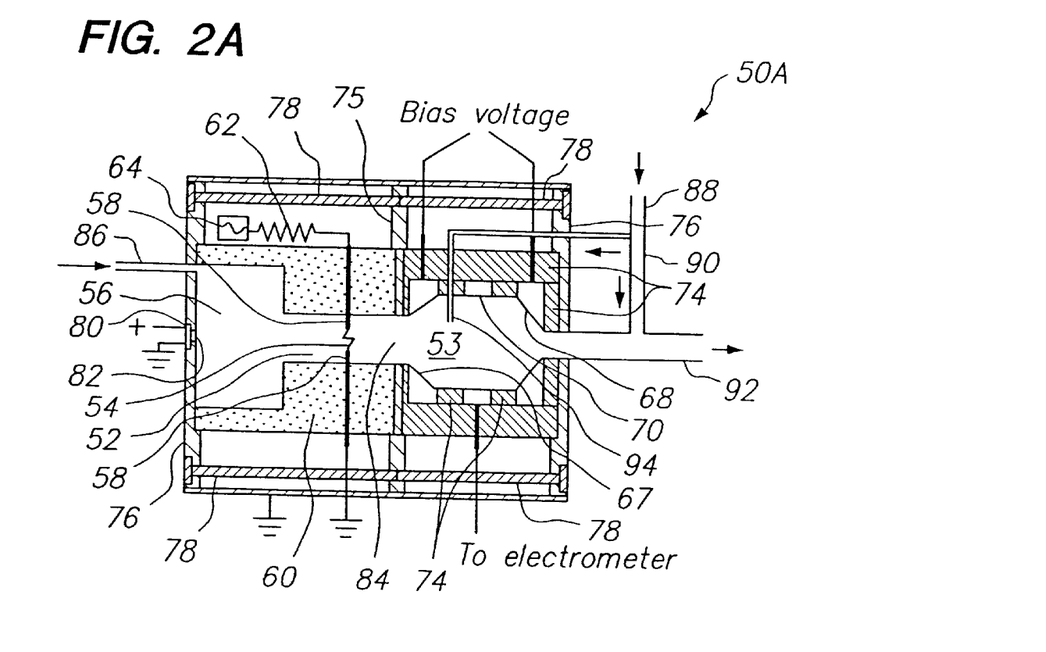
FIGS. 2A to 2D are cross-sectional views of sensors in accordance with alternative embodiments of the invention.

FIGS. 2A to 2D show some alternative embodiments of sensor 50 of FIG. 1. Referring to FIG. 2A, a sensor 50A has an inlet 86 for the working gas, an inlet 88 for sample gas, and an outlet 92 for both the working gas and the sample gas. In operation, the working gas that flows in inlet 86 enters a buffer 56 before reaching a discharge chamber 52. Buffer 56 reduces turbulence that the inflow of working gas might cause in discharge chamber 52. Working gas from discharge chamber 52 flows into an ionization chamber 53 and out outlet 92. As described further below, the flow of sample gas into ionization chamber 53, the flow of working gas into discharge chamber 52, and the geometry of discharge chamber 52 and ionization chamber 53 prevents gas from ionization chamber 53 flowing into discharge chamber 52. This configuration helps prevent contamination of discharge electrodes 58.

Two discharge electrodes 58 are in discharge chamber 52 and separate by a gap of about 0.5 mm to about 2 mm. During operation, AC power supply 64 generates a high AC voltage difference across discharge electrodes 58. In this embodiment, AC high voltage power supply 64 is integrated into sensor 50A. A resistor 62 connects AC power supply 64 to one discharge electrode 64, and the other discharge electrode is grounded. Resistor 62 damps the discharge current. AC power supply 64 initializes and then maintains an AC discharge in the gap between electrodes 58. In the exemplary embodiment, AC power supply 64 provides a 500 to 2500 volt signal with a frequency of 10 Hz to 10 kHz, and preferably between 50 kHz and 500 kHz. Since the direction of electric field and current in the AC discharge alternates between two discharge electrodes 58, discharge electrodes 58 are self-cleaning. A grounded metallic housing 76 of sensor 50a shields the surroundings from the effects of the AC spark, and a grounded electrode 75 shields the ionization chamber 53.

In a discharge zone 54 of discharge chamber 52, the AC discharge creates active species including UV photons and metastable particles that can pass through a passage 84 into ionization chamber 53. Passage 84 allows photons and neutral particles to pass from discharge chamber 52 to ionization chamber 53. Ions created in discharge chamber 54 are generally too short lived to reach ionization chamber 53. Further, grounded electrode 75 between discharge chamber 52 and ionization chamber 53 blocks these ions. Metastable species such as metastable atoms of the working gas, which are electrically neutral, can pass electrode 75 and enter ionization chamber 53. In ionization chamber 53, photons and metastable particles from discharge chamber 52 interact with the sample gas.

In the exemplary embodiment, a body 60 of discharge chamber 52 and buffer 56 is made of a solid insulating material, such as glass, ceramic, or sapphire. Discharge electrodes 58 are made of a noble metal, such as platinum or gold, or a metal coated with the noble metal to resist chemical reactions. The diameter (or cross-sectional area) of discharge chamber 52 is slightly smaller than that of ionization chamber 53 to reduce the diffusion of sample gas into discharge chamber 52. Also, the continuous flow of the working gas from buffer 56 toward discharge zone 54 prevents the sample gas from flowing into discharge chamber 52. In addition, both ends of ionization chamber 53 are conical to reduce the dead volume where sample gas might remain in ionization chamber 51 for extended periods.

Sensor 50A further includes a light detector 80 and a light aperture 82. Light detector 80 is a device such as a photodiode that monitors the intensity and stability of light emitted from the AC discharge. The applied voltage or working gas flow rate can be adjusted if necessary to maintain a desired level of light emissions.

Inside ionization chamber 53, sensor 50A includes two bias electrodes 67 and 68 and a collecting electrode 70. Bias electrodes 67 and 68 create an electric field that accelerates positive ions toward a negative collecting electrode 70. In some embodiments, one bias electrode 67 is adequate. Collecting electrode 70 is coupled to an electrometer (not shown). The electrometer measures a current that the collected ions cause and sends the current to I/V converter 158 (FIG. 1). Electrodes 67, 68, and 70 are typically made of a metal, such as a stainless steel, or the metal coated with a noble metal, such as platinum or gold. Insulating blocks 74 between bias electrodes 67 and 68 and collecting electrode 70 are made of an insulating material such as TEFLON™ (a trademark of Dupont), glass, ceramic, or sapphire. Metallic screws 78 hold parts of sensor 50A together.

Sensor 50A includes unique features for introducing sample gas into ionization chamber 5S. A sample gas inlet 88 from sampling system 152 (FIG. 1) intakes the sample gas, for example, from the surrounding ambient. A splitter divides the sample gas flow into two channels 90 and 94. Channel 90 directs the bulk of sample gas from inlet 88 to an outlet 92, where this portion of the sample gas is exhausted without passing through ionization chamber 53. Channel 94 is a capillary 94 that extends into ionization chamber 53 and directs a small portion of the sample gas into ionization chamber 53. This portion of the sample gas enters a region of ionization chamber 53 that is between first bias electrode 67 and collecting electrode 70 where the ionizing agents from discharge chamber can ionize components of the sample gas. A pump (not shown) exhausts the sample and working gas from ionization chamber 53.

In an exemplary embodiment of the invention, discharge chamber 52 and ionization chamber 53 are predominantly cylindrical with respective diameters of 2.0 mm and 4.0 mm. The flow rate through sample gas inlet 88 is about 500 ml/min, with 499.5 ml/min being directed through channel 90 to outlet 92 and 0.5 ml/min a being directed through channel 94 to ionization chamber 53. The working gas flow rate through inlet 86 is about 1 ml/min. Accordingly, the total exhaust rate out of outlet 92 is about 501 ml/min. The high flow rate through outlet 92 moves the sample gas quickly, and makes possible the real-time monitoring of VOCs and ionizable inorganic gas molecules in the sample gas.

Figure 2B:
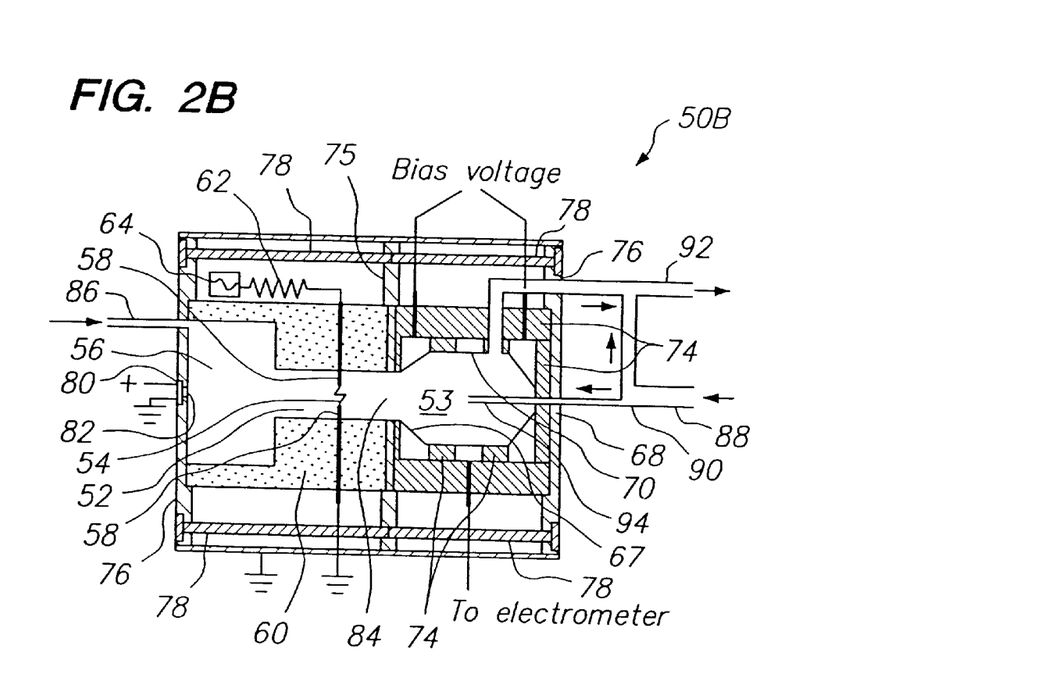
Figure 2C:
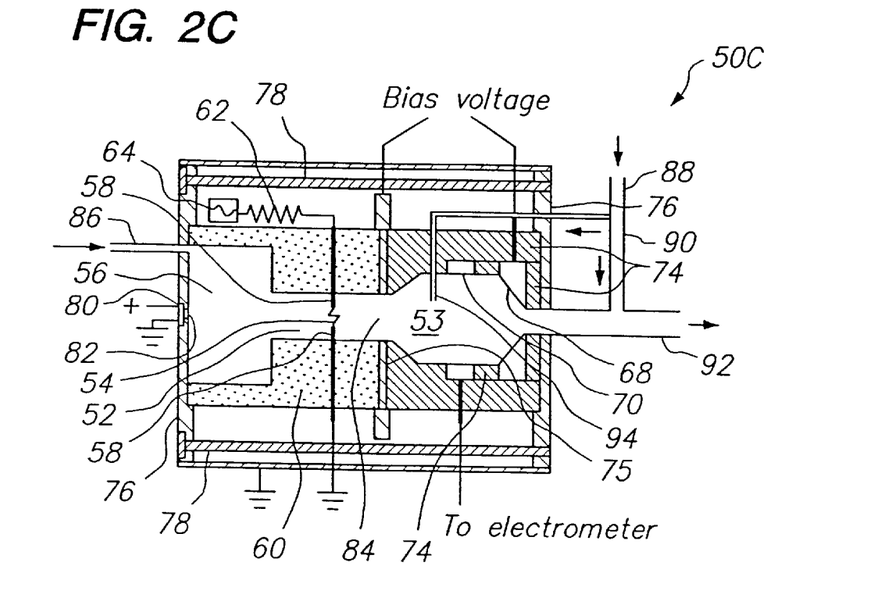
Figure 2D:
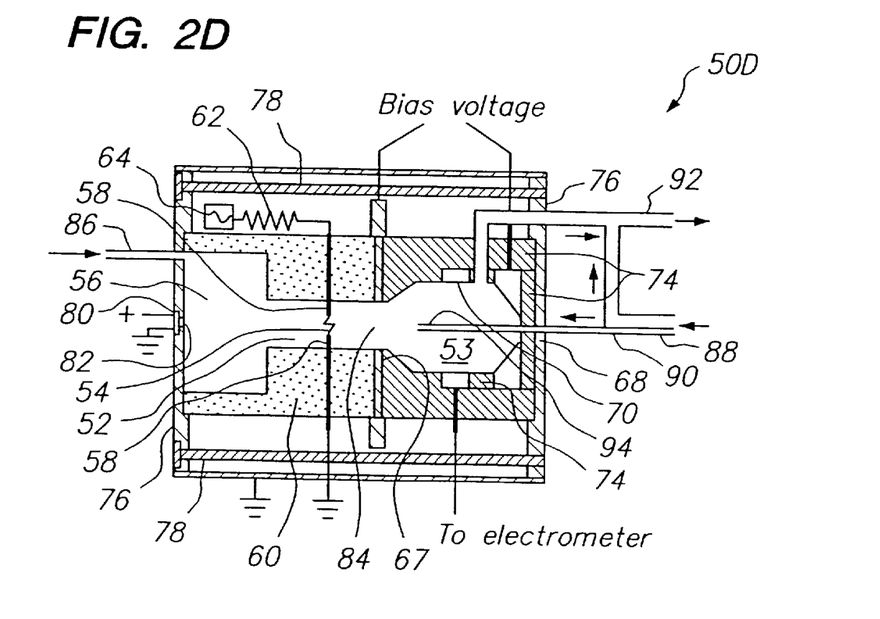

FIGS. 2B, 2C, and 2D illustrate sensors according to alternative embodiments of the invention. In particular, FIG. 2B shows a sensor 50B that differs from sensor 50A of FIG. 2A, in the configuration of the pneumatic system for introducing sample gas into ionization chamber 53 and removing sample and working gases from ionization chamber 53. In sensor 50B, capillary 94 introduces the sample gas coaxially from the end of ionization chamber 53 and removes gas radially from the side of ionization chamber 53. Sensor 50A introduces the sample gas radially from the side of ionization chamber 53 and removes gas coaxially from an end of ionization chamber 53. FIG. 2C shows a sensor 50C that differs from sensor 50A of FIG. 2A in omitting the bias electrode 67 of sensor 50A. Sensor 50C uses electrode 75 as a bias electrode to repel ions created in ionization chamber 53, to shield ionization chamber from the AC discharge, and to block entry of ions from discharge chamber 52 into ionization chamber 53. FIG. 2D shows a sensor 50D that introduces the sample gas coaxially as in sensor 50B of FIG. 2B and uses electrode 75 as a bias electrode as in FIG. 2C.

In the exemplary embodiment of the invention, AC power supply 64 includes a DC/AC converter (not shown). The DC input voltage for the converter is 3 to 15 volts, and the AC output signal of the converter has a 500 to 2500 volt peak depending on the input voltage. A typical frequency range for the AC output signal is 50 kHz to 500 kHz. Changing the DC input voltage changes the peak voltage of the AC output signal. Therefore, a closed loop control circuit such as illustrated in FIG. 3 can change the intensity of the AC discharge to improve the long-term stability of the AC discharge.

Figure 3:
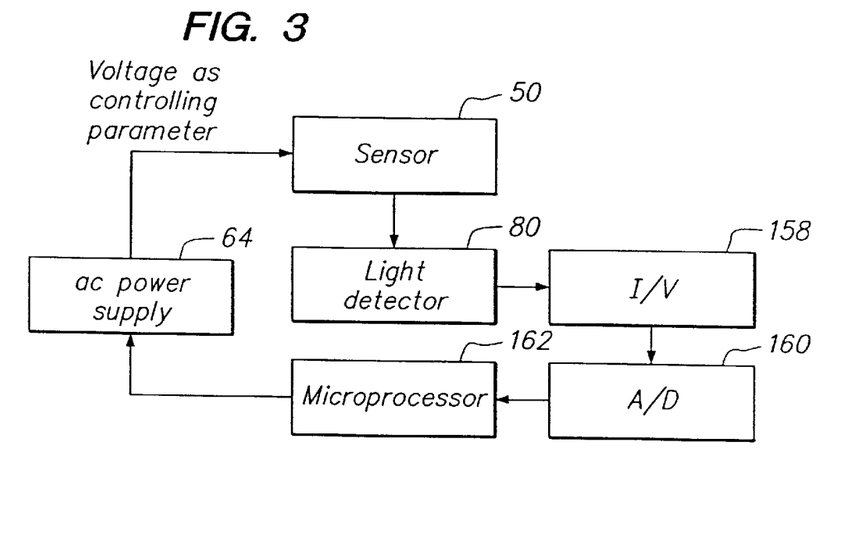
FIG. 3 is a block diagram of a control system for an AC discharge source for an ACDID in accordance with an embodiment of the invention.

Referring to FIG. 3, as mentioned with reference to FIG. 2A, light detector 80, e.g., a photodiode, monitors the light intensity from the AC discharge. Light detector 80 provides a current that is proportional to the light intensity to I/V converter 158. I/V converter 158 converts the signal from light detector 80 to a signal having a voltage proportional to light intensity, and the A/D converter 160 converts that signal to a digital signal for microprocessor 162. Based on the digital signal, microprocessor 162 adjusts or maintains the input DC voltage of AC power supply 64 and hence regulates the AC output voltage of AC high voltage power supply 64. Typically, microprocessor 162 increases the DC voltage to compensate for drops in the measured light intensity and thereby maintains the long-term stability of the AC discharge. Further, starting the AC discharge requires a higher voltage than does maintaining the AC discharge. Accordingly, after starting the AC discharge, microprocessor 162 can reduce the AC voltage to a suitable level for sustaining the AC discharge.

Figure 4:
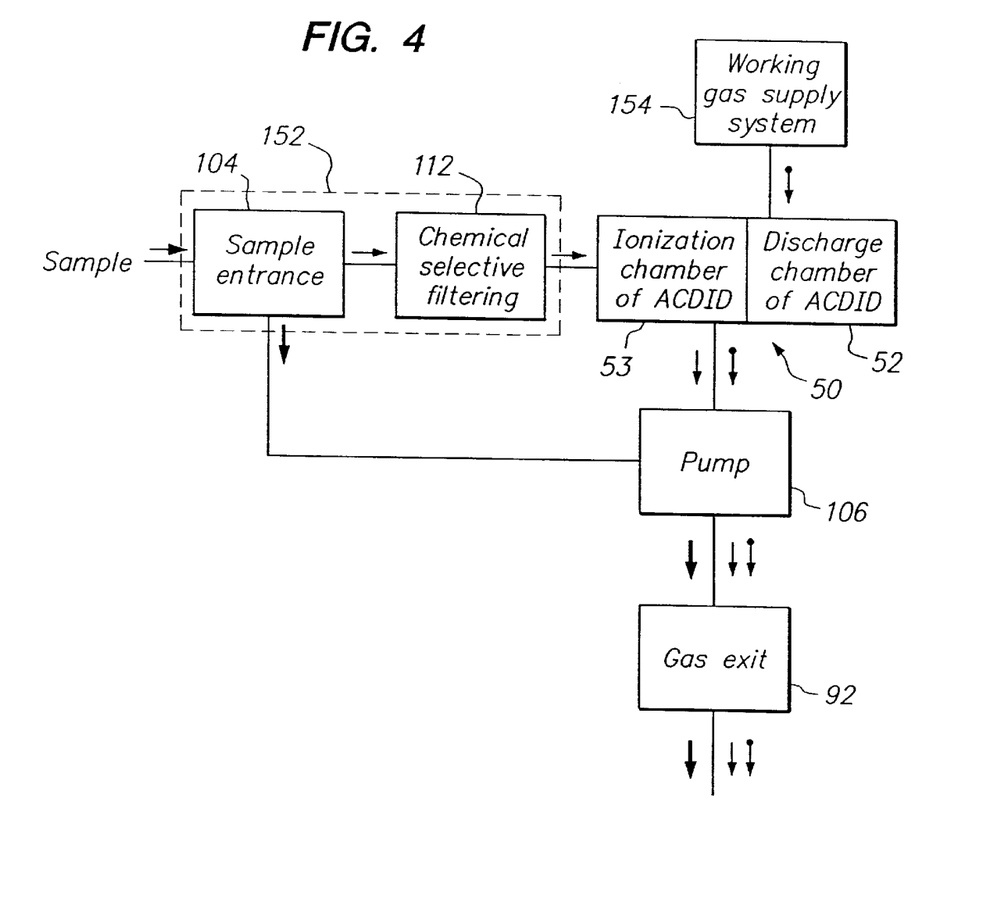
FIG. 4 is a block diagram illustrating gas flow in an ACDID in accordance with an embodiment of the invention.

FIG. 4 is a block diagram of a pneumatic system 100 that supplies sample gas and working gas to sensor 50. Working gas passes into discharge chamber 53 of sensor 50 from working gas supply 154 and from there enters ionization chamber 53. Sampling system 152, which includes a sample entrance 104 and a filter 112, directs sample gas into two channels as described referring to FIG. 2A or 2B. The larger portion of the sample gas travels directly to a pump 106 and then out through gas outlet 92. The smaller portion of the sample gas travels through filter 112 into ionization chamber 53 of sensor 50. Pump 106 removes the sample gas and working gas from ionization chamber 53. In the exemplary embodiment, pump 106 is a rotary vane type pump that can pump continuously and steadily without an oscillation of the gas stream. A piston type pump could cause oscillations of the gas stream inside discharge chamber 52 and thus may undesirably Affect the stability of the AC discharge.

Chemical filter 112, which is upstream of sensor 50, is optional. Chemical filter 112 passes selected components of the sample gas while blocking other components. For example, a suitable chemical filter can let benzene (the target gas) pass while blocking other VOCs such as n-butane, iso-butane, diethyl benzene, ethyl benzene, toluene and other similar VOCs. Chemical filter 112 can be selected according to the target gases to be detected and the other gases that are suspected components of the sample gas. In one embodiment, filter 112 passes the target gases into ionization chamber 53 for measurement and blocks the other gases that would interfere with measurement of the target gases. Selective detection using chemical filters is described further below. In FIG. 4, chemical filter 112 is located after the sample gas is split. This increases the lifetime of chemical filter 112 by reducing the amount of sample gas filtered. However, chemical filter 112 could be before the split.

In accordance with the present invention, the flow rate of working gas through sensor 50 is low enough (e.g., about 1 ml/min), that a small cylinder of working gas provides a long operating time for sensor 50. For example, at a flow rate of 2 ml/min, a 50 ml-1800 psi cylinder can continuously operate for about 100 hours. The low flow rate is practical because the ACDID of the invention uses electric discharge as an ionization source. This is an advantage of the ACDID over FIDs that uses chemical flame discharge as an ionization source. Typically, a higher working gas flow rate is necessary to sustain a chemical flame.

As described above, the working gas for the AC discharge is typically an inert gas, such as helium, argon, krypton, or xenon. The energies of resonant emission lines of argon, krypton and xenon are about 11.7 eV, 10.6 eV, and 9.8 eV, respectively. These energies are less than the ionization potentials of the common components of air, such as nitrogen, oxygen, water, and carbon dioxide. Therefore, the discharges from argon, krypton, or xenon can be used to detect VOCs and some inorganic gases in air if the VOCs and inorganic gases have IPs lower than or equal to the energies of resonant emission lines of argon, krypton, or xenon. Helium has of a high energy resonant emission lines (about 18 eV) and can ionize most components of air as well as VOCs and inorganic gases. Accordingly, helium is not suitable as a working gas for real-time gas detecting in air or any carrier gas having components with IPs below 18 eV because helium cannot distinguish a target gas from the components in the carrier gas. However, if the target gas has been separated from the matrix, for example, by gas chromatography, then helium can be used as a working gas to measure the quantity of the target gas. (The carrier gas for such gas chromatography must be helium.)

Figure 5:
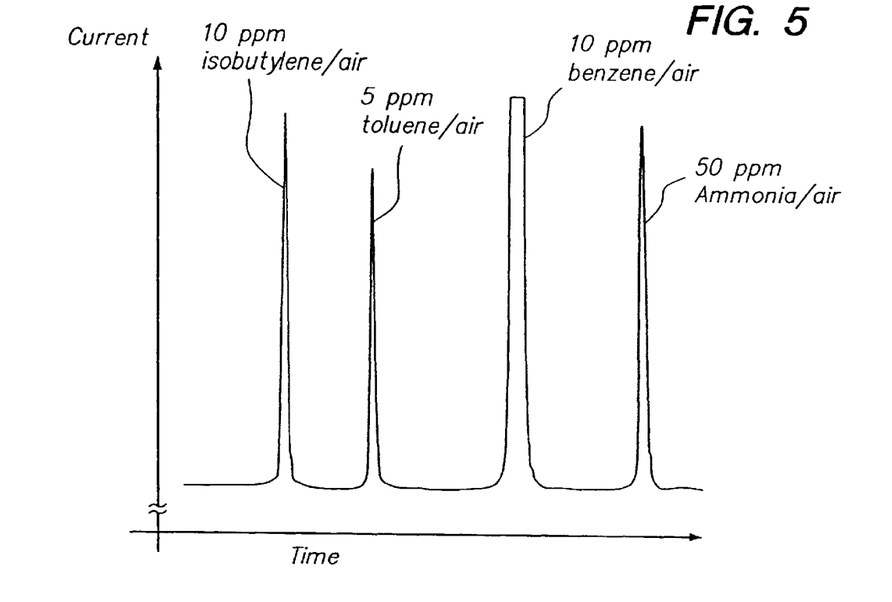
FIG. 5 shows an example of a signal indicating the presence and amount of volatile organic compounds (VOCs) and ionizable inorganic gases.

FIG. 5 shows an example of a current signal resulting when some VOCs and ammonia gas are sequentially mixed into air passing through an ACDID in accordance with an embodiment of the invention. The ACDID uses argon as a working gas and can accordingly identify isobutylene, toluene, benzene, or ammonia in air. The height of each peak depends on the concentration of the target gas and on the efficiency with which the ACDID ionizes and detects the particular target gas. In FIG. 5, the respective concentrations of isobutylene, toluene, benzene, and ammonia are 10 ppm, 5 ppm, 10 ppm, and 50 ppm.

Alternatively, the real-time monitoring of multiple target gases can use multiple working gases and/or multiple sensors to distinguish the different target gas from each other. An illustrative example of a real-time monitoring process presumes that a sample gas may contain toluene (IP=8.82 eV), hexane (IP=10.13 eV), and propane (IP=10.95 eV) in air and that no other ionizable gases are present. The monitoring process of the ACDID changes the working gas periodically and measures ion currents for each of the working gases.

In one such monitoring process, the ACDID initially uses argon as the working gas. The discharge energy level (11.7 eV) of argon ionizes toluene, hexane, and propane, and the ion current signal of the ACDID indicates the gross quantity of all three VOCs components. The microprocessor in the ACDID converts the measured current signal to a toluene equivalent concentration A. The conversion to the equivalent concentration accounts for variables associated with the working gas (initially argon) and is useful for comparisons with equivalent concentrations determined using other working gases. The appropriate formula for such conversion can be determined empirically using sample gases having known concentrations of toluene.

The ACDID then changes the working gas to krypton. The discharge energy level (10.6 eV) of krypton ionizes toluene and hexane but does not ionize propane. Accordingly, the measured ion current signal indicates the quantity of hexane and toluene in the sample gas. The microprocessor converts the measured ion current signal to a toluene equivalent concentration B. The difference between the toluene equivalent concentrations A and B, that is, (A−B), depends on the amount of propane present. Accordingly, the microprocessor can convert the difference (A−B) to a propane equivalent concentration X, using an empirically determined conversion factor or formula.

The ACDID then changes the discharge gas to xenon. The discharge energy level (9.8 eV) of xenon ionizes toluene but cannot ionize hexane or propane. Accordingly, the ion current signal measured then indicates the quantity of toluene present. The microprocessor converts this ion current signal to toluene equivalent concentration C. The difference (B−C) between the toluene equivalent concentrations B and C indicates the quantity of hexane present. Accordingly, the microprocessor converts the difference (B−C) to a hexane equivalent concentration Y. As a result, X, Y, and C are the concentrations of propane, hexane, and toluene, respectively.

Alternatively, the process uses multiple sensors in parallel with different working gases in the various sensors. With this method, the detector simultaneously measures currents indicating the equivalent concentrations A, B, and C. The calculation performed is otherwise the same as above.

Selective real-time detection of multiple VOCs and ionizable gases can also be obtained using chemical filters. In one embodiment of the invention, a chemical filter passes only the target gas from the mixture of multiple VOCs and ionizable gases and retains other components of the mixture. Accordingly, the ion current signal is due to the target gas, and concentration of the target gas is obtained directly. Alternatively, the chemical filter retains only the target gas while letting other components pass. In this case, an ion current is determined for the sample gas without filtering and for the sample gas after filtering. The difference between the two currents indicates the ion current that the target gas causes and therefore indicates the concentration of the target gas in the sample gas.

Figure 6:
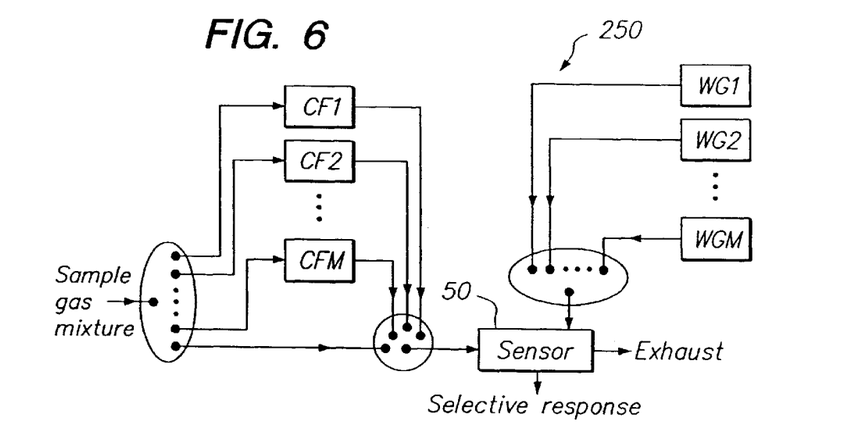
FIG. 6 is a block diagram of an ACDID having multiple working gases and chemical filters in accordance with another embodiment of the invention.

FIG. 6 illustrates an ACDID 250 in accordance with another embodiment of the present invention. ACDID 250 includes a sensor 50 connected to a working gas supply having canisters for multiple working gases WGS1 to WGSm and a sampling system including multiple chemical filters CF1 to CFn. When a sample gas contains a mixture of VOCs and ionizable gases, chemical filters CF1 to CFn can be employed in sequence for measurements of ion currents corresponding to a particular component or components of the sample gas mixture. Also, a control system in ACDID can select and use a particular working gas or gases WG1 to WGm for one or more ion current measurements also using the selected chemical filter or filters. Accordingly, many possible combinations of chemical filters CF1 to CFn and working gases WG1 to WGm can enable selective detection of target gases in the sample gas mixture.

Figure 7:
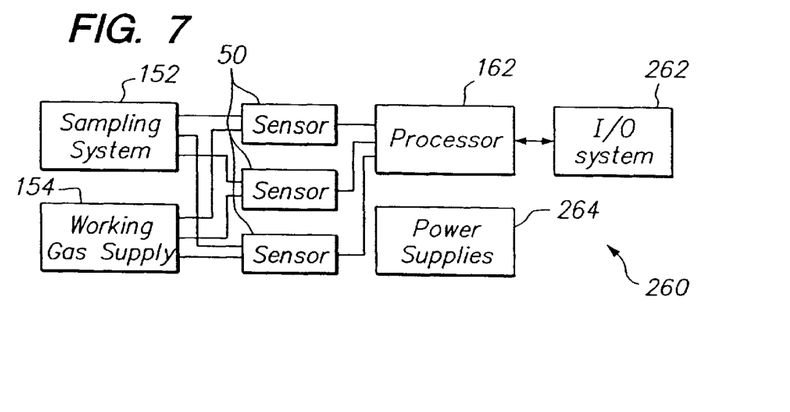
FIG. 7 is a block diagram of an ACDID including multiple sensors in accordance with an embodiment of the invention.

In accordance with a further aspect of the present invention, an ACDID can include multiple sensors 50. FIG. 7 shows an ACDID 260 that includes multiple sensors 50. ACDID 260 simultaneously uses all or some of the sensors 50 to detect particular target gases. In this embodiment, each of sensors 50 can use zero, one, or multiple chemical filters and a single or multiple working gages. In particular, sampling system 152 provides sample gas to all sensors 50. The sample gas can be the same for each sensor 50, or different filters (not shown) can filter an input gas to provide different sample gases to sensors 50. Similarly, working gas supply 154 provides either a different working gas to each sensor 50 of the same working gas to all sensors 50. Processor 152 controls operation of detector 260 and processes current signals from sensors 50 to identify specific target gases. Power supply 264 supplies the AC voltage to drive AC discharge in sensors 50. The peak AC voltage levels for sensors 50 can be individually selected for stability in each sensor.

Aspects of the invention including use of multiple chemical filters, multiple working gases, or multiple sensors can be employed in the ACDIDs as described and also in DCDIDs to selectively detect a target gas in a sample gas mixture.

In summary, according to the present invention, an ACDID, which uses AC discharge as an ionization source, can monitor real-time volatile organic compounds (VOCs) and some ionizable inorganic gases in air. The ACDID has several advantages over other types of ionization detectors. In comparison to an FID, the ACDID uses a safe gas rather than an explosive gas such as hydrogen. In addition, the ACDID has the lower working gas flow rate than does an FID and can operate for a longer time than an FID could with a given working gas supply.

In comparison to a PID, the ACDID does not have a sealed lamp or a window between the ionization source and the ionization chamber. Accordingly, the ACDID avoids the problems of working gas leakage from a sealed lamp, window deterioration, and external surface contamination. The ACDID thus avoids the window-related problems that shorten the lifetimes of PIDs.

Conventional DCDIDs from fixed-direction electric fields between discharge electrodes and thus consume one of the discharge electrodes faster than the other, reducing the stability and lifetime of the DCDID. However, since the ACDID forms an electric field that alternates from one direction to the opposite direction between the discharge electrodes, both electrodes are subject to the same sputtering and deposition. The lives of discharge electrodes are long because deposition and sputtering effects tend to cancel each other. Additionally, as the AC voltage oscillates, discharges stops during two periods when the voltage difference across the discharge electrodes falls below the level required to maintain the discharge. As a result, the discharge electrodes rest twice per cycle of the AC voltage. The rest periods also extend the life of the discharge electrodes.

Although the invention has been described with reference to particular embodiments, the description is only an example of the invention's application and should not be taken as a limitation. Various adaptations and combinations of features of the embodiments disclosed are within the scope of the invention as defined by the following claims.

We claim:

1. A gas detector comprising:
   a sensor comprising:
      a buffer chamber;
      an ionization chamber; and
      a discharge chamber disposed between and coupled to the buffer chamber and the ionization chamber, the discharge chamber including discharge electrodes;
   a working gas supply coupled to the sensor to introduce a working gas into the buffer chamber; and
   an alternating current power supply coupled to drive the discharge electrodes,
   wherein the ionization chamber is positioned to receive active species that result when the AC power supply drives an electric discharge through the working gas, and wherein the active species ionize a sample gas introduced in the ionization chamber.

2. The detector of claim 1, further comprising ail electrode that when biased inhibits ions from flowing from the discharge chamber into the ionization chamber.

3. The detector of claim 1, further comprising:
   a collecting electrode disposed to collect ions generated in the ionization chamber; and
   an electrometer coupled to measure a current due to ions that the collecting electrode collects.

4. The detector of claim 3, further comprising a grounding electrode between the discharge chamber and the ionization chamber, wherein grounding electrode shields the ionization chamber so that the AC discharge does not interfere with current measurements.

5. The detector of claim 1, wherein the working gas includes an inert gas.

6. The detector of claim 5, wherein the working gas is selected from a group consisting of helium, argon, krypton, and xenon.

7. The detector of claim 1, further comprising a sampling system that introduces the sample gas into the ionization chamber.

8. The detector of claim 7, wherein the sampling system comprises:
   a sample gas inlet;
   an outlet;
   a splitter coupled to the sample gas inlet;
   a first channel between the splitter and the ionization chamber;
   a second channel between the splitter and the outlet; and
   a third channel between the ionization chamber and the outlet.

9. The detector of claim 8, wherein the first channel is a capillary that is smaller than the second channel.

10. The detector of claim 7, wherein the sampling system comprises a filter coupled to filter the sample gas before the sample gas enters the ionization chamber.

11. The detector of claim 7, wherein the sampling system comprises:
    a plurality of chemical filters; and
    a system that selects which, if any, of the plurality of chemical filters filter the sample gas before the sample gas enters the ionization chamber.

12. The detector of claim 11, wherein the working gas supply comprises:
    a plurality of different working gases; and
    a system that selects from among the plurality of different working gases, the working gas that is introduced.

13. The detector of claim 7, wherein the sampling system comprises a gas chromatographic column.

14. The detector of claim 7, further comprising a light detector positioned to monitor light from the electric discharge.

15. The detector of claim 1, wherein the working gas supply comprises:
    a plurality of different working gases; and
    a system that selects from among the plurality of different working gases, the working gas that is introduced.

16. The detector of claim 15, wherein for different measurements, the system changes the working gases.

17. A detector comprising:
    working gas supply;
    a sampling system;
    a plurality of sensors coupled to the working gas supply and the sampling system, each sensor comprising:
       a buffer chamber for receiving a working gas from the working gas supply;
       a discharge chamber that receives the working gas from the buffer chamber;
       discharge electrodes in the discharge chamber; and
       an ionization chamber that receives sample gas from the sampling system and active species from the discharge chamber; and
    an alternating current power supply coupled to drive the discharge electrodes in the sensors and thereby create an AC discharge that creates the active species.

18. The detector of claim 17, wherein:
    the working gas supply supplies a plurality of different working gases; and
    for each discharge chamber, the working gas supply selects which of the different working gases the discharge chamber receives.

19. The detector of claim 18, wherein the sampling system includes a filter.

20. The detector of claim 18, wherein:
    the sampling system comprises a plurality of filters; and
    for each ionization chamber, the sampling system selects which of the filters filter sample gas entering the ionization chamber.

21. The detector of claim 17, wherein the sampling system includes a filter.

22. The detector of claim 17, wherein:
    the sampling system comprises a plurality of filters; and
    for each ionization chamber, the sampling system selects which of the filters filter sample gas entering the ionization chamber.

23. A method for detecting a target gas in a sample gas, comprising:
- providing a sensor comprising:
  - a buffer chamber;
  - an ionization chamber; and
  - a discharge chamber disposed between and coupled to the buffer chamber and the ionization chamber, the discharge chamber being narrower than both the buffer chamber and the ionization chamber and including discharge electrodes;
- supplying a first working gas to the buffer chamber of the sensor;
- supplying the sample gas to the ionization chamber of the sensor;
- driving the electrodes with an AC power supply to cause an AC electric discharge between the electrodes whereby the AC electric discharge through the first working gas creates first ionizing agents;
- exposing the sample gas to the first ionizing agents in the ionization chamber; and
- measuring a first current resulting from ions created in the sample gas by the first ionizing agent.

24. The method of claim 23, further comprising:
- supplying a second working gas to the buffer chamber of the sensor;
- driving the electrodes with the AC power supply to cause an AC electric discharge between the electrodes, whereby the AC electric discharge through the second working gas creates second ionizing agents;
- exposing the sample gas to the second ionizing agents in the ionization chamber; and
- measuring a second current resulting from ions created in the sample gas by the second ionizing agents.

25. The method of claim 24, further comprising:
- determining a first concentration of molecules of a first class from the first current;
- determining a second concentration of molecules of a second class from the second current; and
- determining a concentration of the target gas from a difference between the first and second concentrations.

26. The detector of claim 1, wherein the discharge chamber is narrower than both the buffer chamber and the ionization chamber.

* * * * *